(12) United States Patent
Huang et al.

(10) Patent No.: US 11,304,897 B2
(45) Date of Patent: *Apr. 19, 2022

(54) PHARMACEUTICAL FORMULATION CONTAINING UMECLIDINIUM BROMIDE AND VILANTEROL TRIFENATATE

(71) Applicant: ANOVENT PHARMACEUTICAL (U.S.), LLC, Newark, NJ (US)

(72) Inventors: Cai Gu Huang, Shrewsbury, MA (US); Ning He, Shanghai (CN)

(73) Assignee: Anovent Pharmaceutical (U.S.), LLC, Newark, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/342,781

(22) Filed: Jun. 9, 2021

(65) Prior Publication Data

US 2021/0378955 A1 Dec. 9, 2021

Related U.S. Application Data

(60) Provisional application No. 63/036,478, filed on Jun. 9, 2020.

(51) Int. Cl.
*A61K 9/08* (2006.01)
*A61K 31/138* (2006.01)
(Continued)

(52) U.S. Cl.
CPC .............. *A61K 9/08* (2013.01); *A61K 9/0078* (2013.01); *A61K 9/12* (2013.01); *A61K 31/138* (2013.01);
(Continued)

(58) Field of Classification Search
None
See application file for complete search history.

(56) References Cited

U.S. PATENT DOCUMENTS 11,090,294 B2 * 8/2021 Baker ................. A61K 31/439
2011/0251157 A1 10/2011 Pipkin et al.
(Continued)

FOREIGN PATENT DOCUMENTS

| WO | 2004045618 A2 | 6/2004 |
| WO | 2017108917 A1 | 6/2017 |
| WO | 2018036388 A1 | 3/2018 |

OTHER PUBLICATIONS

International Search Report and Written Opinion issued in International Application No. PCT/US2021/036539 as filed on Jun. 9, 2021, and dated Oct. 4, 2021.
(Continued)

*Primary Examiner* — Melissa S Mercier
(74) *Attorney, Agent, or Firm* — Parker Poe Adams and Bernstein LLP

(57) ABSTRACT

The present invention relates to a liquid pharmaceutical preparation and a method for administering the pharmaceutical preparation by nebulizing the pharmaceutical preparation in an inhaler. The propellant-free pharmaceutical preparation comprises: (a) active substances selected from umeclidinium bromide and vilanterol trifenatate; (b) a solvent; (c) a pharmacologically acceptable solubilizing agent; (d) a pharmacologically acceptable preservative; and (e) a pharmacologically acceptable stabilizer; and optionally includes other pharmacologically acceptable additives.

20 Claims, 5 Drawing Sheets

(51) Int. Cl.
    *A61K 47/40*      (2006.01)
    *A61K 9/00*      (2006.01)
    *A61K 47/02*      (2006.01)
    *A61K 9/12*      (2006.01)
    *A61K 47/26*      (2006.01)
    *A61K 31/439*      (2006.01)
    *A61K 47/18*      (2017.01)
    *A61K 47/12*      (2006.01)

(52) U.S. Cl.
    CPC ............ *A61K 31/439* (2013.01); *A61K 47/02* (2013.01); *A61K 47/12* (2013.01); *A61K 47/186* (2013.01); *A61K 47/26* (2013.01); *A61K 47/40* (2013.01)

(56) References Cited

U.S. PATENT DOCUMENTS

| | | |
|---|---|---|
| 2014/0060531 A1 | 3/2014 | Brambilla et al. |
| 2015/0025082 A1 | 1/2015 | Aven et al. |
| 2017/0189424 A1 | 7/2017 | Barnes et al. |
| 2019/0030268 A1 | 1/2019 | Huang |
| 2020/0368214 A1 | 11/2020 | Huang et al. |

OTHER PUBLICATIONS

Abstract of WO2004/045618 A2 with a filing date of Jun. 3, 2004.

* cited by examiner

F m. comp = m comp /M

F m. comp = the mass fraction of the drug substance deposited on each component of the impactor m. comp = mass associated with the component under evaluation M = total mass collected by the system F m. comp = m comp /M F m. comp = the mass fraction of the drug substance deposited on each component of the impactor m. comp = mass associated with the component under evaluation M = total mass collected by the system

PHARMACEUTICAL FORMULATION CONTAINING UMECLIDINIUM BROMIDE AND VILANTEROL TRIFENATATE

PRIORITY STATEMENT

This application claims the benefit of the filing date of U.S. Provisional Patent Application No. 63/036,478, filed on Jun. 9, 2020, which is incorporated herein by reference in its entirety.

BACKGROUND OF THE INVENTION

Umeclidinium bromide, chemically 1-[2-(benzyloxy)ethyl]-4-(hydroxydiphenylmethyl)-1-azoniabicyclo[2.2.2]octane bromide, has the following chemical structure:

Vilanterol trifenatate, chemically triphenylacetic acid-4-{(1R)-2-[(6-{2-[(2,6-dicholorobenzyl)oxy]ethoxy}hexyl)amino]-1-hydroxyethyl}-2-(hydroxymethyl)phenol (1:1), has the following chemical structure:

Umeclidinium is a long acting muscarinic receptor antagonist (also referred to as an anticholinergic). It is a quinuclidine derivative with activity across multiple muscarinic receptor subtypes. Umeclidinium exerts its bronchodilatory activity by competitively inhibiting the binding of acetylcholine with muscarinic receptors on airway smooth muscle. It exhibits slow reversibility at the human M3 muscarinic receptor subtype in vitro and a long duration of action in vivo when administered directly to the lungs in pre-clinical models.

Vilanterol is a selective long-acting, beta2-adrenergic receptor agonist (beta2-adrenergic agonist). The pharmacologic effects of beta2-adrenergic agonists, including vilanterol, are at least in part attributable to their stimulation of intracellular adenylate cyclase, the enzyme that catalyzes the conversion of adenosine triphosphate (ATP) to cyclic-3',5'-adenosine monophosphate (cyclic AMP). Increased cyclic AMP levels causes relaxation of bronchial smooth muscle and inhibition of release of mediators of immediate hypersensitivity from cells, especially from mast cells.

These two compounds have valuable pharmacological properties. Umeclidinium and vilanterol can provide therapeutic benefit in the treatment of asthma or chronic obstructive pulmonary disease, including chronic bronchitis and emphysema.

However, umeclidinium and vilanterol are currently formulated as a dry powder for inhalation with a light grey and red plastic inhaler containing 2 foil blister strips. One strip contains umeclidinium, and the other strip contains vilanterol.

The present invention relates to a propellant-free inhalable formulation of a pharmaceutically acceptable salt of umeclidinium and vilanterol dissolved in water, in conjunction with inactive ingredients that can be administered with a soft mist or nebulization inhalation device, and the propellant-free inhalable aerosols resulting therefrom. The pharmaceutical formulations are especially suitable for administration using a soft mist inhalation or nebulization device, which have much better lung deposition (typically up to 55-60%, even up to 85-95%) compared to administration using a dry powder inhalation device.

The pharmaceutical formulation of the present invention is particularly suitable for administering the active substances by soft mist or nebulization inhalation to treat asthma and chronic obstructive pulmonary disease.

SUMMARY OF THE INVENTION

The present invention relates to pharmaceutical formulations of umeclidinium and vilanterol and their pharmaceutically acceptable salts or solvates which can be administered by soft mist or nebulization inhalation. The pharmaceutical formulations according to the invention meet high quality standards.

One aspect of the present invention is to provide an aqueous pharmaceutical formulation containing umeclidinium and vilanterol, which meets the high standards needed in order to achieve optimum nebulization of the formulation using the inhalers mentioned hereinbefore. Pharmaceutical stability of active substance formulation is a storage time of some years. In one embodiment, the storage time is at least one year. In one embodiment, the storage time is at least three years.

Another aspect is to provide propellant-free formulations that are solutions containing umeclidinium and vilanterol which are nebulized under pressure using an inhaler. In one embodiment, the inhaler is a soft mist or nebulization inhaler device and the composition delivered by the aerosol produced by the inhaler device falls reproducibly within a specified range for particle size of the aerosol. In one embodiment, the particle size is less than about 10 µm.

Another aspect of the invention is to provide pharmaceutical formulations of nebulization solutions comprising umeclidinium and vilanterol and inactive excipients that can be administered by nebulizing the solution using an ultra-sonic based or air pressure-based nebulizer/inhaler. The pharmaceutical stability of the formulation is a storage time of at least a few months. In one embodiment, the storage time is at least 1 month. In one embodiment, the storage time is at least 6 months. In one embodiment, the storage time is at least one year. In one embodiment, the storage time is at least three years.

More specifically, another aspect is to provide a stable pharmaceutical formulation of an aqueous solution containing umeclidinium and vilanterol and other excipients which can be administered by soft mist inhalation using atomizer inhalers. The inventive formulation has substantially long term stability. In one embodiment, the storage temperature of the formulation is from about 1° C. to about 30° C. In one embodiment, the storage temperature of the formulation is from about 15° C. to about 30° C. In one embodiment, the storage temperature of the formulation is below about 15° C. In one embodiment, the storage temperature of the formulation is from about 2° C. to about 8° C.

More specifically, another aspect of the current invention is to provide stable pharmaceutical formulations containing umeclidinium and vilanterol and other excipients which can be administered by nebulizing the formulation using an ultrasonic, jet, or mesh nebulizer. The inventive formulations have substantially long term stability. In one embodiment, the storage temperature of the formulation is from about 1° C. to about 30° C. In one embodiment, the storage temperature of the formulation is from about 15° C. to about 30° C. In one embodiment, the storage temperature of the formulation is below about 15° C. In one embodiment, the storage temperature of the formulation is from about 2° C. to about 8° C.

DETAILED DESCRIPTION OF THE INVENTION

Figure 1:
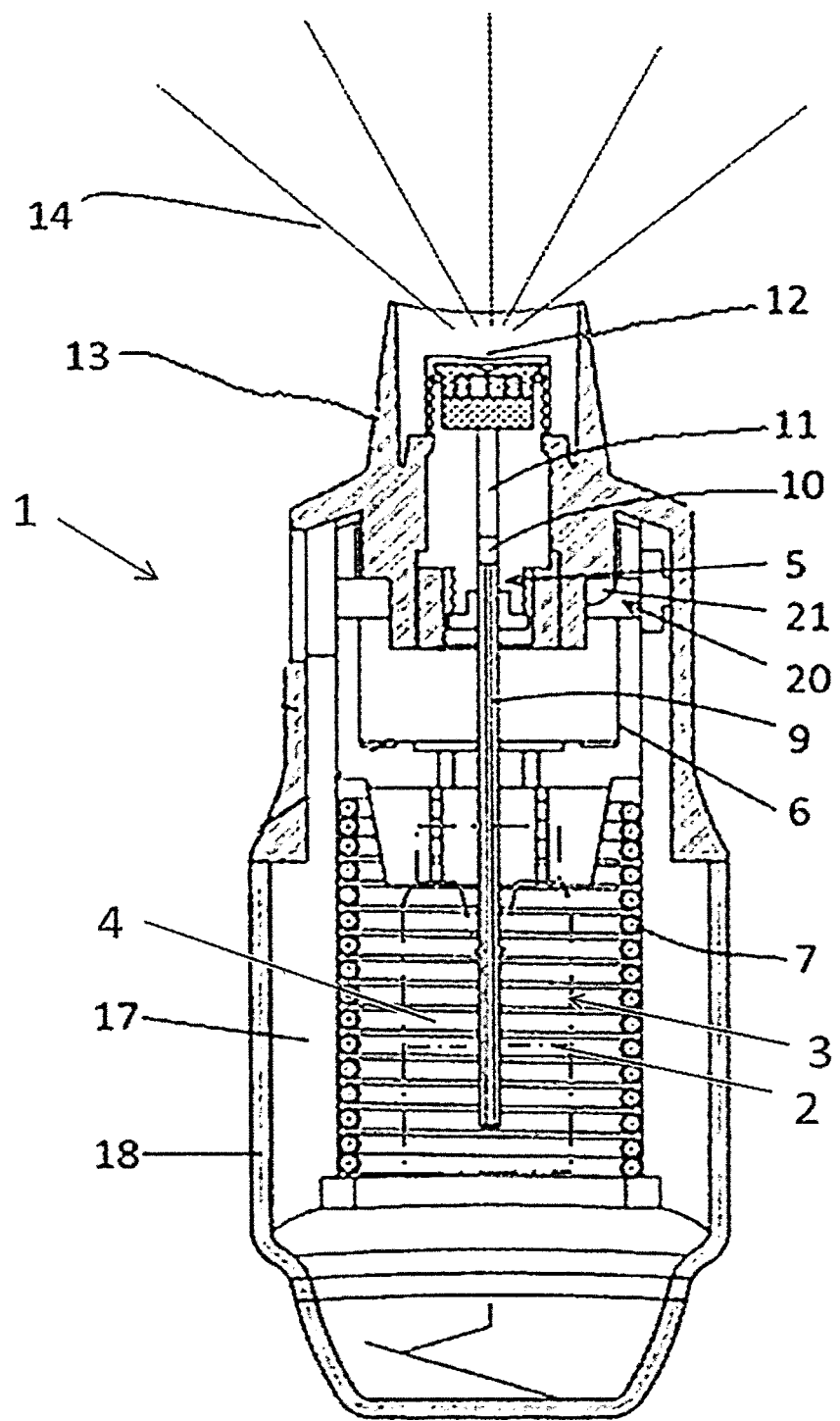
FIG. 1 shows a longitudinal section through the atomizer in the stressed state.

A liquid formulation without propellant gases administered using suitable inhalers achieves better delivery of active substances to the lungs. It is very important to increase the lung deposition of a drug delivered by inhalation.

Currently, traditional pMDI or DPI (dry powder inhalation) can only deliver about 20-35% of a drug to the lungs, resulting in a significant amount of drug being deposited on the month and throat, which can go into the stomach and cause unwanted side effects and or secondary absorption through the oral digestive system.

There is a need to improve the delivery of drugs by inhalation by increasing lung deposition. The soft mist or nebulization inhalation device disclosed in US20190030268 significantly increases the lung deposition of inhalable drugs.

Those inhalers can nebulize a small amount of a liquid formulation within a few seconds into an aerosol that is suitable for therapeutic inhalation. Those inhalers are particularly suitable for use with the liquid formulations provided herein.

In one embodiment, the soft mist or mini-nebulization devices useful for administering the aqueous pharmaceutical formulations of the invention are those in which an amount of less than about 70 microliters of pharmaceutical formulation can be nebulized in one puff so that the inhalable part of aerosol corresponds to the therapeutically effective quantity. In one embodiment, less than about 30 microliters of pharmaceutical formulation can be nebulized in one puff so that the inhalable part of aerosol corresponds to the therapeutically effective quantity. In one embodiment, less than about 15 microliters of pharmaceutical formulation can be nebulized in one puff so that the inhalable part of aerosol corresponds to the therapeutically effective quantity. In one embodiment, the average particle size of the aerosol formed from one puff is less than about 15 microns. In one embodiment, the average particle size of the aerosol formed from one puff is less than about 10 microns.

In one embodiment, the nebulization devices used to administer the pharmaceutical formulations of the invention are those in which an amount of less than 8 milliliters of pharmaceutical solution can be nebulized in one puff, so that the inhalable part of aerosol corresponds to the therapeutically effective quantity. In one embodiment, an amount of less than about 2 milliliters can be nebulized in one puff, so that the inhalable part of aerosol corresponds to the therapeutically effective quantity. In one embodiment, an amount of less than about 1 milliliter can be nebulized in one puff, so that the inhalable part of aerosol corresponds to the therapeutically effective quantity. In one embodiment, the average particle size of the aerosol formed from one puff is less than about 15 microns. In one embodiment, the average particle size of the aerosol formed from one puff is less than about 10 microns.

A device of this kind for the propellant-free administration of a metered amount of a liquid pharmaceutical composition for inhalation is described in detail in, for example, US20190030268 entitled "inhalation atomizer comprising a blocking function and a counter".

The pharmaceutical formulation is converted by the nebulizer into an aerosol destined for the lungs. The pharmaceutical formulation is sprayed with the nebulizer by high pressure.

The pharmaceutical solution is stored in a reservoir in this kind of inhaler. The formulation must not contain any ingredients which might interact with the inhaler to affect the pharmaceutical quality of the formulation or of the aerosol produced. In addition, active substances in the pharmaceutical formulations are very stable when stored and can be administered directly.

The formulations of the current invention for use with the inhaler described above may contain additives, such as the disodium salt of edetic acid (sodium edetate), to reduce the incidence of spray anomalies and to stabilize the formulation. The formulations preferably have a minimum concentration of sodium edetate.

One aspect of the present invention is to provide a pharmaceutical formulation containing umeclidinium and vilanterol and other excipients, which meets the high standards needed in order to achieve optimum nebulization using a soft mist inhaler. In one embodiment, the formulation has a storage time of at least a few months or years. In one embodiment, the formulation has a storage time of at least about 1 month. In one embodiment, the formulation has a storage time of at least about 6 months. In one embodiment, the formulation has a storage time of at least about one year. In one embodiment, the formulation has a storage time of at least about three years.

Another aspect of the current invention is to provide propellant-free formulations that are solutions containing umeclidinium and vilanterol which can be nebulized under pressure using an inhaler. In one embodiment, the inhaler is a the soft mist inhaler or a nebulization inhaler. In one embodiment, the aerosol produced by the inhaler falls reproducibly within a specified range for particle size. In one embodiment, the particle size is less than about 10 µm.

Another aspect of the invention is to provide an aqueous pharmaceutical formulation that is a solution containing umeclidinium and vilanterol and other inactive excipients that can be administered by inhalation.

The phrase "umeclidinium or a salt or solvate thereof," as used herein, means umeclidinium containing any pharmaceutically acceptable counterion and pharmaceutically acceptable solvates thereof. The phrase "vilanterol or a salt or solvate thereof," as used herein, means any pharmaceutically acceptable salt or solvate of vilanterol. The terms umeclidinium and vilanterol, as used herein, is to be taken as referring to umeclidinium or a salt or solvate thereof and to vilanterol or a salt or solvate thereof, respectfully.

In one embodiment, the pharmaceutical formulation contains umeclidinium bromide. In one embodiment, the pharmaceutical formulation contains vilanterol trifenatate.

In one embodiment, the active substances are a combination of umeclidinium bromide and vilanterol trifenatate.

In one embodiment, the umeclidinium and vilanterol are dissolved in a solvent. In one embodiment, the umeclidinium and vilanterol are dissolved water. In one embodiment, umeclidinium bromide and vilanterol trifenatate are dissolved in a solvent. In one embodiment, umeclidinium bromide and vilanterol trifenatate are dissolved in water.

The concentration of the umeclidinium and vilanterol in the finished pharmaceutical formulation depends on the desired therapeutic effect. In one embodiment, the concentration of umeclidinium in the formulation ranges from about 2 mg/100 ml to about 1050 mg/100 ml. In one embodiment, the concentration of umeclidinium in the formulation ranges from about 10 mg/100 ml to about 600 mg/100 ml. In one embodiment, the concentration of umeclidinium in the formulation ranges from about 20 mg/100 ml to about 350 mg/100 ml. In one embodiment, the concentration of vilanterol in the formulation ranges from about 1 mg/100 ml to about 550 mg/100 ml. In one embodiment, the concentration of vilanterol in the formulation ranges from about 5 mg/100 ml to about 300 mg/100 ml. In one embodiment, the concentration of vilanterol in the formulation ranges from about 10 mg/100 ml to about 200 mg/100 ml.

In one embodiment, a therapeutically effective dose of umeclidinium bromide ranges from about 1 µg to about 130 µg. In one embodiment, a therapeutically effective dose of umeclidinium bromide ranges from about 5 µg to about 120 µg. In one embodiment, the daily dose of umeclidinium bromide ranges from about 16 µg to about 112 micrograms. In one embodiment, a therapeutically effective dose of umeclidinium bromide ranges from about 30 µg to about 80 µg. In one embodiment, a therapeutically effective dose of umeclidinium bromide ranges from about 40 µg to about 60 µg. In one embodiment, a therapeutically effective dose of umeclidinium bromide is about 56 µg. In one embodiment, a therapeutically effective dose of vilanterol trifenatate ranges from about 1 µg to about 100 µg. In one embodiment, a therapeutically effective dose of vilanterol trifenatate ranges from about 5 µg to about 80 µg. In one embodiment, a therapeutically effective dose of vilanterol trifenatate ranges from about 9 µg to about 60 µg. In one embodiment, a therapeutically effective dose of vilanterol trifenatate ranges from about 20 µg to about 40 µg. In one embodiment, a therapeutically effective dose of vilanterol trifenatate is about 30 µg. In one embodiment, the daily dose of umeclidinium bromide is about 55.7 micrograms and the daily dose of vilanterol trifenatate is about 30 micrograms.

In one embodiment, the soft mist devices used to administer the pharmaceutical formulations of the present invention can atomize about 10 to about 15 microliters, 1 to 4 times per use, so that the inhalable part of the aerosol corresponds to the therapeutically effective quantity.

In one embodiment, the formulations include an acid or base as a pH adjusting agent. In one embodiment, the pH adjusting agent is selected from the group consisting of hydrochloric acid, citric acid or its buffer and/or the salts thereof.

Other pH adjusting agents can be used in the present invention. In one embodiment, the pH adjusting agents is sodium hydroxide.

The pH of the formulation is selected so as to ensure the stability of the formulation. In one embodiment, the pH ranges from about 2.0 to about 6.0. In one embodiment, the pH ranges from about 3.0 to about 5.0. In one embodiment, the pH ranges from about 4.0 to about 5.0.

In one embodiment, the formulations include edetic acid (EDTA) or one of the known salts thereof, disodium edetate, or edetate disodium dihydrate as a stabilizer or complexing agent. In one embodiment, the formulation contains edetic acid and/or a salt thereof.

Other comparable stabilizers or complexing agents can be used in the formulations of the present invention. Examples of other stabilizers or complexing agents include, but are not limited to, citric acid, edetate disodium, and edetate disodium dihydrate.

The phrase "complexing agent," as used herein means a molecule which is capable of entering into complex bonds. Preferably, these compounds should have the effect of complexing cations. In one embodiment, the concentration of the stabilizer or complexing agent ranges from about 1 mg/100 ml to about 500 mg/100 ml. In one embodiment, the concentration of the stabilizer or complexing agent ranges from about 5 mg/100 ml to about 200 mg/100 ml. In one embodiment, the stabilizer or complexing agent is edetate disodium dihydrate in a concentration of about 10 mg/100 ml.

In one embodiment, all the ingredients of the formulation are present in solution.

The term "additive," as used herein means any pharmacologically acceptable and therapeutically useful substance which is not an active substance, but can be formulated together with the active substances in the pharmacologically suitable solvent, in order to improve the qualities of the active substance formulation. Preferably, these additives have no appreciable pharmacological effect or, at least no undesirable pharmacological effects in the context of the desired therapy.

Suitable additives include, but are not limited to, other stabilizers, complexing agents, antioxidants, surfactants, and/or preservatives that prolong the shelf life of the finished pharmaceutical formulation, vitamins, and/or other additives known in the art.

Preservatives protect the formulation from contamination with pathogenic bacteria. Suitable preservatives include, but are not limited to, benzalkonium chloride, benzoic acid, and sodium benzoate. In one embodiment, the formulation contains benzalkonium chloride as the only preservative. In one embodiment, the amount of the preservative ranges from about 2 mg/100 ml to about 300 mg/100 ml. In one embodiment, the preservative is benzalkonium chloride is an amount of about 10 mg/100 ml.

In one embodiment, the formulations include a solubility enhancing agent, such as Tween 80 or a cyclodextrin derivative. In one embodiment, the solubility enhancing agent is a cyclodextrin derivative or a salt thereof. The solubility enhancing agent improves solubility of the active ingredients or other excipients. In one embodiment, the solubility enhancing agent is sulfobutylether β-cyclodextrin or a salt thereof.

In one embodiment of the soft mist inhalation formulations, the formulation includes a surfactant or other solubility enhancing agent, such as Tween 80 (polysorbate 80) or a cyclodextrin derivative. In one embodiment, the surfactant or other solubility enhancing agent is present in an amount ranging from about 1 g/100 ml to about 40 g/100 ml. In one embodiment, the surfactant or other solubility enhancing agent is present in an amount ranging from about 10 g/100 ml to about 30 g/100 ml. In one embodiment, the surfactant or other solubility enhancing agent is present in an amount ranging from about 15 g/100 ml to about 25 g/100 ml. In one embodiment, the surfactant or other solubility enhancing agent is a cyclodextrin derivative or a salt thereof. In one embodiment, the surfactant or other solubility enhancing agent is sulfobutylether β-cyclodextrin. In one embodiment, the sulfobutylether β-cyclodextrin is present in an amount ranging from about 1 g/100 ml to about 40 g/100 ml. In one embodiment, the sulfobutylether β-cyclodextrin is present in an amount ranging from about 10 g/100 ml to about 30 g/100 ml. In one embodiment, the sulfobutylether β-cyclodextrin is present in an amount ranging from about 15 g/100 ml to about—25 g/100 ml.

Another aspect of the invention is to provide stable pharmaceutical soft mist formulations containing umeclidinium and vilanterol and other excipients which can be administered by soft mist inhalation using atomizer inhalers. In one embodiment, the storage temperature of the formulation is from about 1° C. to about 30° C. In one embodiment, the storage temperature of the formulation is from about 15° C. to about 30° C. In one embodiment, the storage temperature of the formulation is below about 15° C. In one embodiment, the storage temperature of the formulation is from about 2° C. to about 8° C.

Another aspect of the invention is to provide pharmaceutical formulations of nebulization solutions comprising umeclidinium and vilanterol and other inactive excipients which can be administered by nebulization inhalation using an ultra-sonic based or air pressure based nebulizer/inhaler. In one embodiment, the storage temperature of the formulation is from about 1° C. to about 30° C. In one embodiment, the storage temperature of the formulation is from about 15° C. to about 30° C. In one embodiment, the storage temperature of the formulation is below about 15° C. In one embodiment, the storage temperature of the formulation is from about 2° C. to about 8° C.

Another aspect of the invention is to provide stable pharmaceutical formulations containing umeclidinium and vilanterol and other excipients which can be administered by nebulization inhalation using an ultra-sonic based or air pressure-based nebulizer/inhaler. The formulations have substantially long-term stability. In one embodiment, the storage temperature of the formulation is from about 1° C. to about 30° C. In one embodiment, the storage temperature of the formulation is from about 15° C. to about 30° C. In one embodiment, the storage temperature of the formulation is below about 15° C. In one embodiment, the storage temperature of the formulation is from about 2° C. to about 8° C.

In one embodiment, the formulations include sodium chloride. In one embodiment, the concentration of sodium chloride ranges from about 0.1 g/100 ml to about 0.9 g/100 ml.

In one embodiment, the concentration of umeclidinium in the nebulization formulation ranges from about 7 mcg/2 ml to about 3700 mcg/2 ml. In one embodiment, the concentration of umeclidinium in the nebulization formulation ranges from about 35 mcg/2 ml to about 1800 mcg/2 ml. In one embodiment, the concentration of umeclidinium in the nebulization formulation ranges from about 50 mcg/2 ml to about 100 mcg/2 ml. In one embodiment, the concentration of vilanterol in the nebulization formulation ranges from about 4 mcg/2 ml to about 2000 mcg/2 ml. In one embodiment, the concentration of vilanterol in the nebulization formulation ranges from about 20 mcg/2 ml to about 1000 mcg/2 ml. In one embodiment, the concentration of vilanterol in the nebulization formulation ranges from about 30 mcg/2 ml to about 50 mcg/2 ml.

In one embodiment, the formulations for nebulization include a surfactant or other solubility enhancing agent, such as Tween 80 or a cyclodextrin derivative. In one embodiment, the surfactant or other solubility enhancing agent is a cyclodextrin derivative or a salt thereof. In one embodiment, the surfactant or other solubility enhancing agent is sulfobutylether β-cyclodextrin.

It has been found that sulfobutylether β-cyclodextrin not only enhances solubility, but advantageously improves stability of active ingredients.

Another aspect of the current invention is to provide stable pharmaceutical formulations for nebulization containing umeclidinium and vilanterol and other excipients which can be administered by soft mist inhalation using an atomizer inhaler or by nebulization inhalation using an ultrasonic based or air pressure based nebulizer/inhaler. The formulations have substantially long-term stability. In one embodiment, the formulations have a storage time of at least about 6 months at a temperature of from about 15° C. to about 25° C. In one embodiment, the formulations have a storage time of at least about 12 months at a temperature of from about 15° C. to about 25° C. In one embodiment, the formulations have a storage time of at least about 24 months at a temperature of from about 15° C. to about 25° C. In one embodiment, the formulations have a storage time of at least about 36 months at a temperature of from about 15° C. to about 25° C.

The pH of the formulation influences the stability and solubility of the umeclidinium and vilanterol in the formulation. The pH can be adjusted to the desired value by adding an acid, e.g., HCl, or by adding a base, e.g., NaOH.

In one embodiment, the pH of the nebulization formulation ranges from about 3 to about 6. In one embodiment, the pH of the nebulization formulation ranges from about 3 to about 5. In one embodiment, the pH of the nebulization formulation ranges from about 4 to about 5.

The nebulization formulations according to the present invention can be filled into canisters to provide a highly stable formulation for use in a nebulization device. The formulations exhibit substantially no particle growth, change in morphology, or precipitations. There also is no, or substantially no, problem of suspended particles being deposited on the surface of the canister or valves, so that the formulations can be discharged from a suitable nebulization device with high dose uniformity. Suitable nebulizers include, but are not limited to, an ultrasonic nebulizer; a jet nebulizer; a mesh nebulizer, such as a Pari eFlow nebulization inhaler; or other commercially available ultrasonic nebulizer, jet nebulizer, or mesh nebulizer.

In one embodiment, the inhalation device is a soft mist inhaler. To produce the aerosols, the pharmaceutical soft mist formulation containing umeclidinium and vilanterol is preferably administered using an inhaler of the kind described herein. Here, we once again expressly mention the patent documents described hereinbefore, to which reference is hereby made, and which is incorporated by reference.

A soft mist inhaler device of this kind for the propellant-free administration of a metered amount of a liquid pharmaceutical formulation for inhalation is described in detail, for example, in US20190030268 entitled "inhalation atomizer comprising a blocking function and a counter".

The pharmaceutical formulation is a solution that is converted by the nebulizer into an aerosol destined for the lungs. The nebulizer uses high pressure to spray the pharmaceutical solution.

The soft mist inhalation device can be carried anywhere by the patient, since it has a cylindrical shape and a handy size of less than about 8 cm to 18 cm long and 2.5 cm to 5 cm wide. The nebulizer sprays a defined volume of the pharmaceutical formulation out through small nozzles at high pressures, so as to produce inhalable aerosols.

The preferred atomizer comprises an atomizer 1, a fluid 2, a vessel 3, a fluid compartment 4, a pressure generator 5, a holder 6, a drive spring 7, a delivering tube 9, a non-return valve 10, pressure room 11, a nozzle 12, a mouthpiece 13, an aerosol 14, an air inlet 15, an upper shell 16, and an inside part 17.

The inhalation atomizer 1 comprising the block function and the counter described above for spraying a medicament fluid 2 is depicted in FIG. 1 in a stressed state. The atomizer 1 comprising the block function and the counter described above is preferred as a portable inhaler and requires no propellant gas.

FIG. 1 shows a longitudinal section through the atomizer in the stressed state.

For the typical atomizer 1 comprising the block function and the counter described above, an aerosol 14 that can be inhaled by a patient is generated through the atomization of the fluid 2, which is preferably formulated as a medicament liquid. The medicament is typically administered at least once a day, more specifically multiple times a day, preferably at predetermined time gaps, according to how seriously the illness affects the patient.

In an embodiment, the atomizer 1 described above has substitutable and insertable vessel 3, which contains the medicament fluid 2. A reservoir for holding the fluid 2 is formed in the vessel 3. Specifically, the medicament fluid 2 is located in the fluid compartment 4 formed by a collapsible bag in the vessel 3.

In an embodiment, the amount of fluid 2 for the inhalation atomizer 1 described above is in the vessel 3 to provide, e.g., up to 200 doses. A typical vessel 3 has a volume of about 2 ml to about 10 ml. A pressure generator 5 in the atomizer 1 is used to deliver and atomize the fluid 2 in a predetermined dosage amount. The fluid 2 can be released and sprayed in individual doses, specifically from about 5 to about 30 microliters.

In an embodiment, the atomizer 1 described above may have a pressure generator 5 and a holder 6, a drive spring 7, a delivering tube 9, a non-return valve 10, a pressure room 11, and a nozzle 12 in the area of a mouthpiece 13. The vessel 3 is latched by the holder 6 in the atomizer 1 so that the delivering tube 9 is plunged into the vessel 3. The vessel 3 can be separated from the atomizer 1 for substitution.

In an embodiment, when drive spring 7 is stressed in an axial direction, the delivering tube 9, the vessel 3 along with the holder 6 will be shifted downwards. Then the fluid 2 will be sucked into the pressure room 11 through delivering tube 9 and the non-return valve 10.

In one embodiment, after releasing the holder 6, the stress is eased. During this process, the delivering tube 9 and closed non-return valve 10 are shifted back upward by releasing the drive spring 7. Consequently, the fluid 2 is under pressure in the pressure room 11. The fluid 2 is then pushed through the nozzle 12 and atomized into an aerosol 14 by the pressure. A patient can inhale the aerosol 14 through the mouthpiece 13, while the air is sucked into the mouthpiece 13 through air inlets 15.

The inhalation atomizer 1 described above has an upper shell 16 and an inside part 17, which can be rotated relative to the upper shell 16. A lower shell 18 is manually operable to attach onto the inside part 17. The lower shell 18 can be separated from the atomizer 1 so that the vessel 3 can be substituted and inserted.

In one embodiment of the inhalation atomizer 1 described above has a lower shell 18, which carries the inside part 17, and is rotatable relative to the upper shell 16. As a result of rotation and engagement between the upper unit 17 and the holder 6, through a gear 20, the holder 6 is axially moved counter to the force of the drive spring 7, and the drive spring 7 is stressed.

In an embodiment, in the stressed state, the vessel 3 is shifted downwards and reaches a final position, which is demonstrated in FIG. 1. The drive spring 7 is stressed in this final position. Then the holder 6 is clasped. Therefore, the vessel 3 and the delivering tube 9 are prevented from moving upwards so that the drive spring 7 is stopped from easing.

In an embodiment, the atomizing process occurs after releasing the holder 6. The vessel 3, the delivering tube 9 and the holder 6 are shifted back by the drive spring 7 to the beginning position. This is referred to herein as major shifting. When major shifting occurs, the non-return valve 10 is closed and the fluid 2 is under pressure in the pressure room 11 by the delivering tube 9, and then the fluid 2 is pushed out and atomized by the pressure.

In an embodiment, the inhalation atomizer 1 described above may have a clamping function. During the clamping, the vessel 3 preferably performs a lifting shift for the withdrawal of fluid 2 during the atomizing process. The gear 20 has sliding surfaces 21 on the upper shell 16 and/or on the holder 6, which can make holder 6 move axially when the holder 6 is rotated relative to the upper shell 16.

In an embodiment, the holder 6 is not blocked for too long and can perform the major shifting. Therefore, the fluid 2 is pushed out and atomized.

In an embodiment, when holder 6 is in the clamping position, the sliding surfaces 21 move out of engagement. Then the gear 20 releases the holder 6 for the opposite axial shift.

Figure 2:
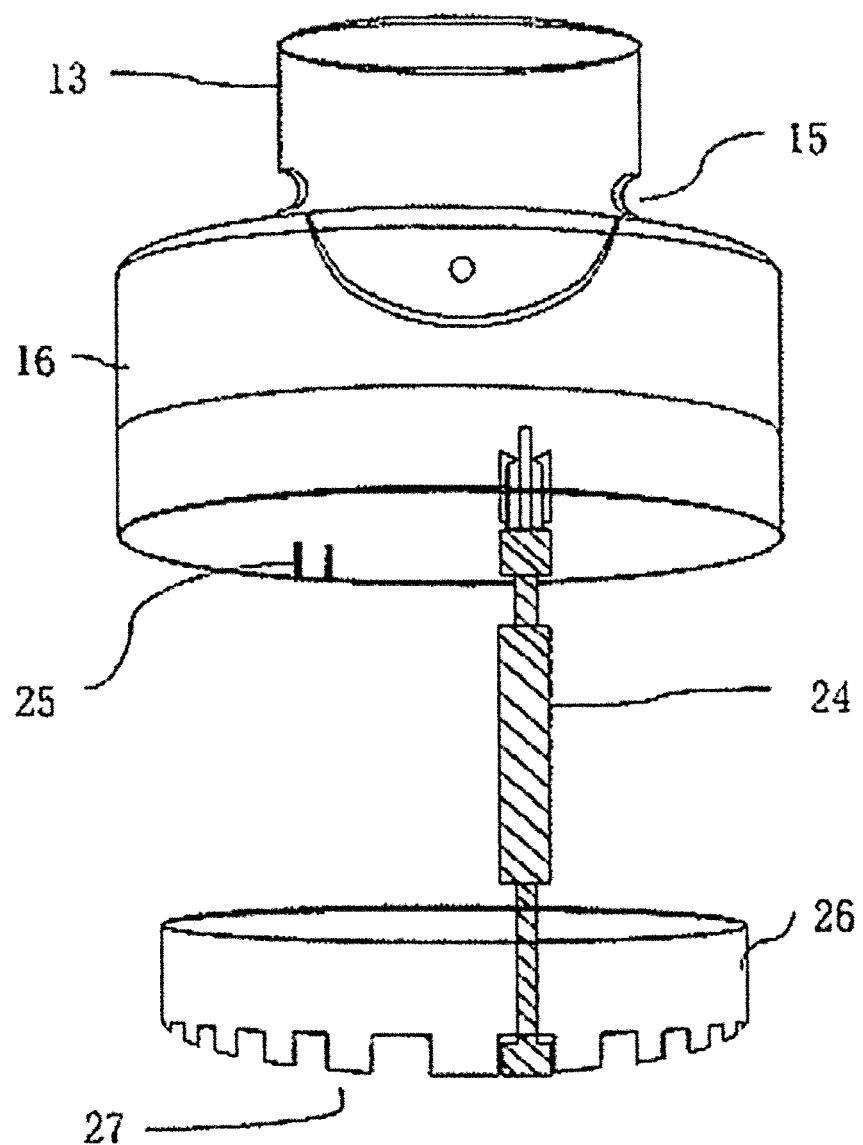
FIG. 2 shows a counter element of the atomizer.
Figure 3:
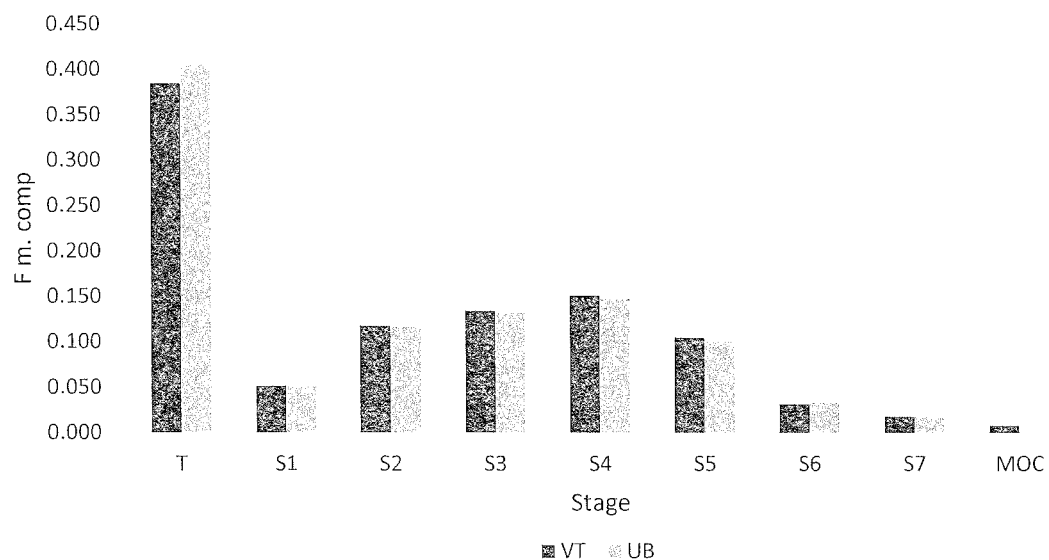
FIG. 3 shows the aerodynamic particle size distribution of vilanterol trifenatate (VT) and umeclidinium bromide(UB) as described in example 4.
Figure 4:
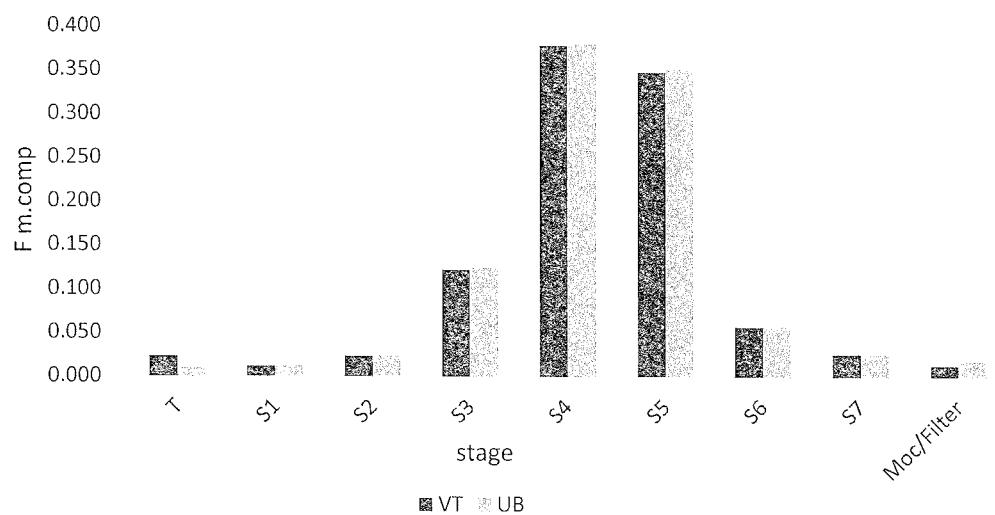
FIG. 4 shows aerodynamic particle size distribution of vilanterol trifenatate (VT) and umeclidinium bromide(UB) as described in example 7.
Figure 5:
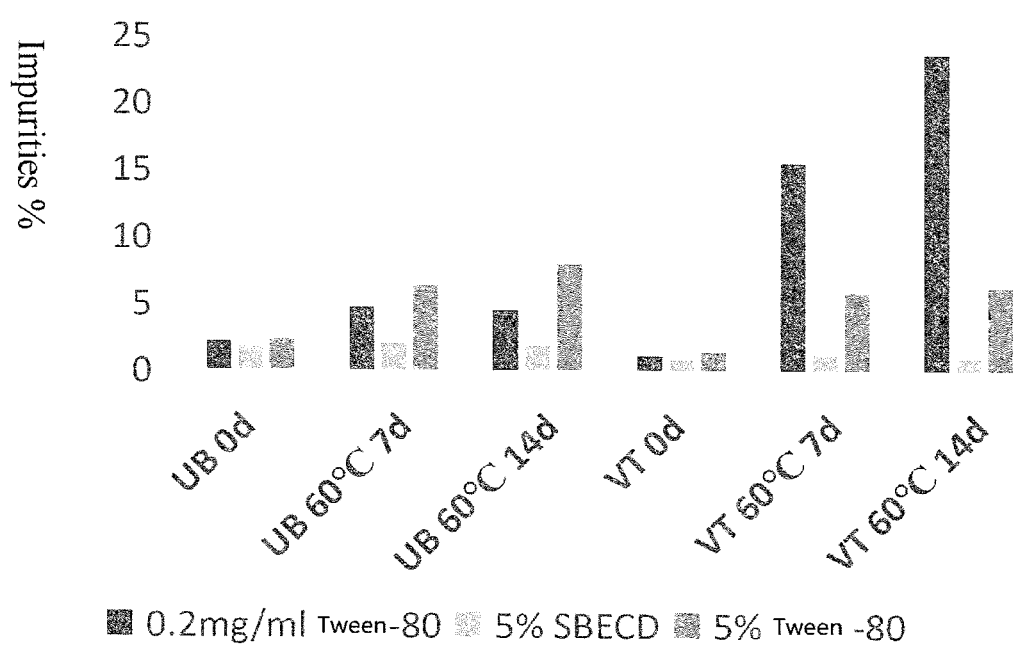
FIG. 5 shows the impurities in samples 1-3 as described in example 11.

In one embodiment, the atomizer 1 includes a counter element as shown in FIG. 2. The counter element has a worm 24 and a counter ring 26. The counter ring 26 is preferably circular and has dentate part at the bottom. The worm 24 has upper and lower end gears. The upper end gear contacts with the upper shell 16. The upper shell 16 has inside bulge 25. When the atomizer 1 is employed, the upper shell 16 rotates; and when the bulge 25 passes through the upper end gear of the worm 24, the worm 24 is driven to rotate. The rotation of the worm 24 drives the rotation of the counter ring 26 through the lower end gear so as to result in a counting effect.

In an embodiment, the locking mechanism is realized mainly by two protrusions. Protrusion A is located on the outer wall of the lower unit of the inside part. Protrusion B is located on the inner wall of counter. The lower unit of the inside part is nested in the counter. The counter can rotate relative to the lower unit of the inside part. Because of the rotation of the counter, the number displayed on the counter can change as the actuation number increases, and can be observed by the patient. After each actuation, the number displayed on the counter changes. Once the predetermined number of actuations is achieved, Protrusion A and Protrusion B will encounter each other and the counter will be prevented from further rotation. Therefore, the atomizer is blocked and stopped from further use. The number of actuations of the device can be counted by the counter.

Atomization devices include, but not limited to, soft mist inhalers, ultra-sonic atomizers, air compression atomizers, and mesh based atomizers.

The soft mist inhaler provides pressure to eject a metered dose drug solution. Two high-speed jets are formed, and the two jets collide with each other to form droplets with smaller particles.

With an ultrasonic atomizer, the oscillation signal of the main circuit board is amplified by a high-power triode and transmitted to the ultrasonic wafer. The ultrasonic wafer converts electrical energy into ultrasonic energy. The ultrasonic energy can atomize the water-soluble drug into tiny mist particles ranging from about 1 µm to about 5 µm at normal temperature. With the help of an internal fan, the medicine particles are ejected.

An air compression atomizer is mainly composed of a compressed air source and an atomizer. The compressed gas is suddenly decompressed after passing through the narrow opening at high speed and a negative pressure is generated locally so that the solution of the active substance is sucked out from the container because of a siphon effect. When subject to high-speed air flow, the solution of active substance is broken into small aerosol particles by collision.

Mesh based atomizers contain a stainless steel mesh covered with micropores having a diameter of about 3 µm. The number of micropores exceeds 1,000. The mesh is conical with the cone bottom facing the liquid surface. Under the action of pressure, the vibration frequency of the mesh is about 130 KHz. The high vibration frequency breaks the surface tension of the drug solution contacted with the mesh and produces a low-speed aerosol.

EXAMPLES

Materials and Reagents:

50% benzalkonium chloride aqueous solution purchased from Merck.

Edetate disodium dihydrate purchased from Merck.

Sodium hydroxide purchased from Titan reagents.

Hydrochloric acid purchased from Titan reagents.

Sodium chloride purchased from Merck.

Sulfobutylether β-cyclodextrin purchased from Zhiyuan Bio-tech Co., Ltd., China.

Umeclidinium purchased from Anhui Dexinjia Pharma Co., Ltd.

Vilanterol purchased from Shengde Pharma Co., Ltd.

Example 1

The preparation of a soft mist inhalation solution (Sample I) is as follows:

50% benzalkonium chloride aqueous solution, edetate disodium dihydrate, and SBECD according to the amounts in Table 1 were dissolved in 90 ml of purified water. Umeclidinium bromide and vilanterol trifenatate according to the amounts in Table 1 were added to the solution and the resulting mixture sonicated until the components completely dissolved. The solution was adjusted to the target pH with hydrochloric acid or sodium hydroxide. Finally, purified water was added to provide a final volume of 100 ml.

TABLE 1

| Components of sample I | |
| --- | --- |
| Ingredients | Sample I |
| Umeclidinium bromide | 37.1 mg |
| Vilanterol trifenatate | 20 mg |
| Sulfobutylether β-Cyclodextrin (SBECD) | 5 g |
| 50% benzalkonium chloride aqueous solution | 20 mg |
| Edetate disodium dihydrate | 10 mg |
| Hydrochloride Acid | To pH 4.0 |
| Purified water | Added to 100 ml |

Example 2

Thermal stability at 60° C. of Sample I of Example 1 is provided below.

TABLE 2

| Thermal Stability at 60° C. of Sample I of Example 1 | | |
| --- | --- | --- |
|  | 0 d | 14d |
| UB-related total impurity | 0.9% | 1.0% |
| VT-related total impurity | 1.8% | 1.9% |

As shown in in Table 2, UB and VT are very stable because adding sulfobutylether β-cyclodextrin.

Example 3

The preparation of a soft mist inhalation solution (Sample II) is as follows:

50% benzalkonium chloride aqueous solution, edetate disodium dihydrate, and SBECD according to the amounts in Table 3 were dissolved in 90 ml of purified water. Umeclidinium bromide and vilanterol trifenatate according to the amounts in Table 3 were added and the resulting mixture sonicated until the components completely dissolved. The solution was adjusted to the target pH with hydrochloric acid or sodium hydroxide. Finally, purified water was added to provide a final volume of 100 ml.

TABLE 3

Components of Sample II

| Ingredients | Sample II |
| --- | --- |
| Umeclidinium bromide | 21 mg |
| Vilanterol trifenatate | 11 mg |
| Sulfobutylether β-Cyclodextrin (SBECD) | 5 g |
| 50% benzalkonium chloride aqueous solution | 20 mg |
| Edetate disodium dihydrate | 10 mg |
| Hydrochloride Acid | To pH 4.0 |
| Purified water | Added to 100 ml |

Example 4

Aerodynamic Particle Size Distribution of the soft mist inhalation solution (Sample II of Example 3):

Sample II was sprayed using a soft mist inhaler. The aerodynamic particle size distribution of the droplets of sample II was measured using a Next Generation Impactor (NGI). The Next Generation Impactor was operated at a flow rate of 30 L/min to determine the particle size distribution. For each of the impactor experiments, the impactor collection stages were coated with a silicone oil. The particle size distribution is expressed in terms of mass median aerodynamic diameter (MMAD) and geometric standard deviation (GSD). The results show that the MMAD of vilanterol trifenatate and umeclidinium bromide were less than 10 μm and that the GSD of vilanterol trifenatate and umeclidinium bromide were less than 5% (Table 4).

TABLE 4

Aerodynamic Particle Size Distribution

| Particle size parameter | vilanterol trifenatate | umeclidinium bromide |
| --- | --- | --- |
| MMAD (μm) | 3.92 | 3.92 |
| GSD (%) | 2.32 | 2.32 |

Example 5

Sample II of Example 3 was sprayed using a soft mist inhalation device. A Malvern Spraytec (STP5313) was used to measure the particle size of the droplets. The results are shown in Table 5.

TABLE 5

Droplet Particle Size Distribution of Sample II of Example 3 Using a Soft Mist Inhaler

| Device No. | Test time | Dv (10) μm | Dv (50) μm | Dv (90) μm |
| --- | --- | --- | --- | --- |
| Device 1 | 1 | 2.6 | 5.4 | 10.2 |
|  | 2 | 2.4 | 4.9 | 9.1 |
|  | 3 | 2.3 | 4.6 | 8.4 |
| Device 2 | 1 | 3.2 | 6.1 | 11.6 |
|  | 2 | 2.8 | 5.3 | 9.6 |
|  | 3 | 2.7 | 5.2 | 9.2 |

Example 6

The preparation of a nebulization inhalation solution (Sample III) is as follows:

Sodium chloride and SBECD according to the amounts in Table 6 were dissolved in 90 ml of purified water. Umeclidinium bromide and vilanterol trifenatate according to the amounts in Table 6 were added and the resulting mixture sonicated until the components completely dissolved. The solution was adjusted to the target pH with hydrochloric acid or sodium hydroxide. Finally, purified water was added to provide a final volume of 100 ml.

TABLE 6

Components of Sample III

| Ingredients | Sample III |
| --- | --- |
| Umeclidinium bromide | 7.4 mg |
| Vilanterol trifenatate | 4.0 mg |
| Sulfobutylether β-Cyclodextrin (SBECD) | 5 g |
| Sodium chloride | 600 mg |
| Hydrochloric acid or sodium hydroxide | To pH 4.0 |
| Purified water | Added to 100 ml |

Example 7

Aerodynamic Particle Size Distribution of nebulization inhalation solution (Sample III of Example 6):

Sample III was sprayed using a soft mist inhaler. The aerodynamic particle size distribution of the droplets of sample III was measured using a Next Generation Impactor (NGI). The Next Generation Impactor was operated at a flow rate of 15 L/min to determine the particle size distribution. For each of the impactor experiments, the impactor collection stages were coated with a silicone oil. The particle size distribution is expressed in terms of mass median aerodynamic diameter (MMAD) and Geometric Standard Deviation (GSD). The results show that the MMAD of vilanterol trifenatate and umeclidinium bromide were less than 10 μm and that the GSD of vilanterol trifenatate and umeclidinium bromide were less than 5% (Table 7).

TABLE 7

Aerodynamic Particle Size Distribution of the Nebulization Inhalation Solution of Sample III of Example 6

| Particle size parameter | vilanterol trifenatate(VT) | umeclidinium bromide(UB) |
| --- | --- | --- |
| MMAD (μm) | 3.48 | 3.48 |
| GSD (%) | 1.55 | 1.55 |

Example 8

The preparation of Sample IV is as follows:

Tween 80 according to the amount in Table 8 was dissolved in 90 ml of purified water. Umeclidinium bromide and vilanterol trifenatate according to the amounts in Table 8 were added to the solution and the resulting mixture sonicated until the components completely dissolved. Finally, purified water was added to provide a final volume of 100 ml.

TABLE 8

Components of Sample IV

| Ingredients | Sample IV |
| --- | --- |
| Umeclidinium bromide | 37.1 mg |
| Vilanterol trifenatate | 20 mg |

TABLE 8-continued

Components of Sample IV

| Ingredients | Sample IV |
| --- | --- |
| Tween 80 | 5 g |
| Purified water | Added to 100 ml |

Example 9

Solubility in Different Cosolvents:

5% tween-80: Dissolve 5 g tween-80 in 100 g purified water.

5% Sulfobutylether β-cyclodextrin: Dissolve 5 g Sulfobutylether β-cyclodextrin in 100 g purified water.

20% Sulfobutylether β-cyclodextrin: Dissolve 20 g Sulfobutylether β-cyclodextrin in 100 g purified water.

TABLE 9

Solubility of UB and VT in Various Solvents

| solvents | UB solubility (µg/ml) | VT solubility (µg/ml) |
| --- | --- | --- |
| purified water | 617.87 | 53.66 |
| 0.2 mg/ml tween-80 | 581.67 | 62.57 |
| 5% tween -80 | 3540.95 | 1370.79 |
| 5% Sulfobutylether β-Cyclodextrin | 3555.20 | 369.66 |
| 20% Sulfobutylether β-Cyclodextrin | 3447.58 | 1399.30 |

As shown in in Table 9, UB and VT are almost insoluble in purified water. When tween-80 and Sulfobutylether β-Cyclodextrin were both added in amounts of 5%, VT was found to be more soluble.

Example 10

The formulation and preparation of nebulization inhalation solutions (samples 1-3) are as follows:

TABLE 10

Components of Samples 1-3

| Ingredients | Sample 1 0.2 mg/ml tween-80 | Sample 2 5% SBECD | Sample 3 5% tween-80 |
|---|---|---|---|
| UB | 3.71 mg | 37.1 mg | 37.1 mg |
| VT | 2 mg | 20 mg | 20 mg |
| Tween-80 | 20 mg | N/A | 5 g |
| SBECD | N/A | 5 g | N/A |
| Purified water | 100 g | 100 g | 100 g |

Sample Preparation Method:

SBECD or tween-80 according to the amounts provided in Table 10 were dissolved in 90 ml of purified water. UB and VT according to the amounts provided in Table 10 were added to the solution and the resulting mixture sonicated until the components completely dissolved. Finally, purified water was added to provide a final weight of 100 g.

Method for Detection of Impurities:

Instrument: HPLC waters J (2695/2996)

Column: ACE Excel 3 C18-FPF V20-3880 150*4.6 mm 3 um

Wavelength: 200 nm

Flow: 0.8 ml/min

Column temperature: 40° C.

Time: 96 min

Mobile phase A: 2.87 g of sodium heptane sulfonate and 2.5 g of sodium dihydrogen phosphate dissolved in 1 L of water and the pH adjusted to pH 4.0 with phosphoric acid.

Mobile phase B: Acetonitrile.

Gradient elution profile:

| Time (min) | Mobile phase A (%) | Mobile phase B (%) |
|---|---|---|
| 0 | 85 | 15 |
| 1 | 85 | 15 |
| 10 | 65 | 35 |
| 15 | 65 | 35 |
| 60 | 48 | 52 |
| 75 | 33 | 67 |
| 85 | 30 | 70 |
| 86 | 85 | 15 |
| 96 | 48 | 15 |

The impurities in samples 1-3 were detected using this method.

TABLE 11

Effect of Solvent Components on Stability

| | Ingredients | | Sample 1 0.2 mg/ml Tween-80 | Sample 2 5% SBECD | Sample 3 5% tween-80 |
|---|---|---|---|---|---|
| 0 day | character | | Colorless clear liquid | | |
| | Total | UB | 2.16 | 1.84 | 2.33 |
| | Impurities % | VT | 1.18 | 0.90 | 1.47 |
| 60° C. | character | | Colorless clear liquid | | |
| 7 day | Total | UB | 4.73 | 2.02 | 6.36 |
| | Impurities % | VT | 15.53 | 1.26 | 5.88 |
| 60° C. | character | | Colorless clear liquid | | |
| 14 | Total | UB | 4.54 | 1.91 | 7.97 |
| day | Impurities % | VT | 23.66 | 1.02 | 6.26 |

As shown in Table 11, UB and VT are more stable in an SBECD-containing solution.

Sulfobutylether beta cyclodextrin sodium significantly improves the solubility of umeclidinium bromide and vilanterol, and provides a dissolution rate that is faster than that of Tween 80 at 0.2 mg/ml.

Comparing the data at 7 d and 14 d, it can be seen that the sodium sulfobutylether beta cyclodextrin significantly improves the stability of the UB-VT solution. There is no significant increase in the content of impurities after being placed at 40° C. or 60° C. for 7 days; there is basically no change from day 0. The solution of UB-VT with Tween-80 has more impurities. Although 5% Tween-80 is better than 0.2 mg/ml, it is less effective than the same concentration of SBECD.

Sulfobutylether beta cyclodextrin sodium is superior to Tween-80 in terms of improving solubility and stability.

Example 11 pH Stability:

The pH of the solution has a large impact on the solubility and stability of vilanterol trifenatate and umeclidinium bromide. We compared the effects of different pH values on stability.

We designed several different formulations and examined the influence of different pH values on the stability of the formulations. The formulations and stability results are shown in the tables below.

TABLE 12

Formulations of UB and VT at Different pH Values

| Ingredients | Sample 4 | Sample 5 | Sample 6 | Sample 7 | Sample 8 |
|---|---|---|---|---|---|
| UB | 10.5 mg | 10.5 mg | 10.5 mg | 10.5 mg | 10.5 mg |
| VT | 5.5 mg | 5.5 mg | 5.5 mg | 5.5 mg | 5.5 mg |
| SBECD | 2.5 g | 2.5 g | 2.5 g | 2.5 g | 2.5 g |
| HCl | Adjusted to pH 2.5 | Adjusted to pH 3.0 | Adjusted to pH 4.0 | Adjusted to pH 5.0 | Not adjust pH |
| Purified water | Added to 50 g | Added to 50 g | Added to 50 g | Added to 50 g | Added to 50 g |

Preparation Method:

SBECD according to the amount provided in Table 12 was dissolved in 40 ml of purified water. UB and VT according to the amounts provided in Table 12 were added to the solution and the resulting mixture sonicated until the components completely dissolved. The solution was adjusted to the target pH shown in Table 12 with hydrochloric acid. Finally, purified water was added to provide a final weight of 50 g.

TABLE 13

Stability at Different pH Values

| | Ingredients | | Sample 4 pH: 2.5 | Sample 5 pH: 3.0 | Sample 6 pH: 4.0 | Sample 7 pH: 5.0 | Sample 8 pH: 6.8 |
|---|---|---|---|---|---|---|---|
| 0 day | character | | Colorless clear liquid | | | | |
| | Content μg/ml | UB | 193.74 | 192.24 | 194.02 | 193.50 | 195.18 |
| | | VT | 106.26 | 106.59 | 106.45 | 106.18 | 107.12 |
| | Impurities % | VT impurity 1 | ND | ND | ND | ND | ND |
| | | VT impurity 2 | 0.05 | 0.05 | 0.05 | 0.04 | 0.08 |
| | | UB Total impurities | 1.82 | 1.81 | 1.82 | 1.87 | 1.80 |
| | | VT Total impurities | 0.89 | 0.87 | 0.88 | 0.96 | 1.23 |
| 60° C. 7 days | character | | Colorless clear liquid | | | | |
| | Content μg/ml | UB | 194.30 | 195.10 | 194.90 | 190.30 | 195.00 |
| | | VT | 103.70 | 105.00 | 106.90 | 104.60 | 96.90 |
| | Impurities % | VT impurity 1 | 0.21 | 0.18 | 0.01 | ND | 1.23 |
| | | VT impurity 2 | 0.59 | 0.49 | 0.03 | 0.04 | 4.30 |
| | | UB Total impurities | 1.78 | 1.69 | 2.30 | 2.26 | 1.84 |
| | | VT Total impurities | 1.56 | 1.35 | 1.46 | 1.36 | 6.69 |
| 60° C. 14 days | character | | Colorless clear liquid | | | | |
| | Content μg/ml | UB | 195.37 | 196.91 | 196.72 | 196.73 | 196.74 |
| | | VT | 101.29 | 103.77 | 107.48 | 107.37 | 93.04 |
| | Impurities % | VT impurity 1 | 0.33 | 0.28 | ND | ND | 1.58 |
| | | VT impurity 2 | 1.03 | 0.83 | 0.07 | 0.06 | 5.76 |
| | | UB Total impurities | 2.54 | 2.34 | 2.54 | 2.47 | 2.15 |
| | | VT Total impurities | 2.97 | 2.52 | 1.67 | 1.61 | 8.81 |

When the solution was prepared at a low pH, there was no obvious change in the solution, indicating that SBECD has a protective and stabilizing effect on vilanterol, preventing the triphenylacetic acid group from being replaced by hydrochloric acid.

By comparing impurity data at 0 days and 7 days, it can be seen that pH 4.0 exhibits the best stability. When the pH is not adjusted the UB-VT content decreases significantly over time and the impurities increase significantly. Thus, it is necessary to adjust the pH to ensure good stability.

At 14 days the content of the active agents shows some increase, which may be a natural error of the analysis. In terms of impurities at 14 days, pH 4.0 and pH 5.0 are better than other pH values, and pH 5.0 is better than pH 4.0.

Example 12

Stability Contrast Experiment

TABLE 14

Components of Samples 9-11

| Ingredients | Sample 9 | Sample 10 | Sample 11 |
|---|---|---|---|
| UB | 5.57 mg | 5.57 mg | 5.57 mg |
| VT | 3 mg | 3 mg | 3 mg |
| SBECD | 2.0 g | 2.0 g | 2.0 g |
| NaCl | 750 mg | 750 mg | 750 mg |
| HCl | Adjusted to pH 4.00 | Adjusted to pH 4.50 | Adjusted to pH 5.00 |
| Purified water | Added to 101.1 g | Added to 101.1 g | Added to 101.1 g |

Preparation Method:

SBECD and NaCl according to the amounts provided in Table 14 were dissolved in 90 ml of purified water. UB and VT according to the amounts provided in Table 14 were added to the solution and the resulting mixture sonicated until the components completely dissolved. The solution was adjusted to the target pH shown in Table 14 with hydrochloric acid. Finally, purified water was added to provide a final weight of 101.1 g.

TABLE 15

The Stability Results of Samples 9-11 (Conditions: 40° C. ± 2° C./75% ± 5% RH)

| | | | 0 day | 1 month | 3 months | 6 months |
|---|---|---|---|---|---|---|
| Sample 9 | Total impurities % | VT | 0.8 | 0.73 | 0.9 | 0.5 |
| | | UB | 1.86 | 2.09 | 2.05 | 2.33 |
| Sample 10 | Total impurities % | VT | 0.84 | 0.78 | 0.78 | 0.51 |
| | | UB | 1.96 | 2.11 | 2.06 | 2.35 |
| Sample 11 | Total impurities % | VT | 0.88 | 0.71 | 0.94 | 0.65 |
| | | UB | 2.36 | 2.06 | 2.43 | 2.39 |

TABLE 16

The Stability Results of Sample 9 (Conditions: 40° C. ± 2° C./75% ± 5% RH)

| | | 0 day | 1 month | 3 months | 6 months |
|---|---|---|---|---|---|
| character | | Colorless clear liquid | | | |
| pH | | 4.00 | 3.96 | 4.03 | 3.96 |
| Osmotic pressure (mOsm) | | 287 | 276 | 272 | 273 |
| Concentration | VT | 29.17 | 29.50 | 30.49 | 28.58 |
| (mg/100 ml) | UB | 56.18 | 54.64 | 54.91 | 53.19 |

TABLE 17

Components of Sample 12

| Ingredients | Sample12 |
|---|---|
| UB | 21 mg |
| VT | 11 mg |
| 50% BAC | 20 mg |
| Tween-80 | 40 mg |
| 95% ethanol | 20 g |
| EDTA | 11 mg |
| Purified water | Added to 100 ml |

Preparation Method:

The components of sample 12 are listed in Table 17. 50% benzalkonium chloride and tween-80 according to the amounts in Table 17 were dissolved in 20 g of 95% by sequentially adding the ethanol in 3 portions of about 6 mL, about 6 mL, and about 8 mL. The resulting solution was then transferred into a 100 ml volumetric flask. Vilanterol trifenatate and umeclidinium bromide according to the amounts in Table 17 were added to the solution and the resulting mixture sonicated until the components completely dissolved. Edetate disodium dihydrate according to the amount in Table 17 was added to the solution and the resulting mixture sonicated until the components completely dissolved. Finally, the flask was made to volume with purified water.

TABLE 19

The Stability Results of Sample 12 (condition: 25° C.)

| Impurities | 1 Month | 2 Months | 3 Months |
|---|---|---|---|
| Total impurities of UB and VT (%) | 3.17 | 3.51 | 4.49 |

TABLE 20

The Stability Results of Sample 12 (condition: 40° C.)

| Impurities | 1 Month | 2 Months | 3 Months |
|---|---|---|---|
| Total impurities of UB and VT(%) | 6.83 | 11.33 | 15.95 |

Comparing the content and impurity data of samples 9-11 with sample 12, the total impurities of samples 12, containing alcohol and Tween-80, increases with time when stored at 25° C. The total impurities at 25° C. after 3 months is 4.49%. When sulfobutylether β-cyclodextrin is added to samples 9-11, the total impurities of the solution are relatively small, about 3% at 25° C. after 3 months, and the total amount of impurities is lower than in sample 12. The total impurities of sample 12 stored at 40° C. for 3 months was 15.95%, whereas the total impurities of samples 9-11 was about 3%, which is a smaller increase compared to sample 12 stored at 25° C. for 3 months. The total impurities were significantly lower when the sample included sulfobutylether β-cyclodextrin. We believe that sulfobutylether β-cyclodextrin can increase the stability of the solution.

Example 13

We compared the aerosols produced from a self-made sample and from Oulaxin powder using a Next Generation Pharmaceutical Impactor (NGI). The results are as follows:

TABLE 18

The Stability Results of Sample 12

| | | 0 day | | 1 Month | | 2 Months | | 3 Months | |
|---|---|---|---|---|---|---|---|---|---|
| | | Concentration mg/100 ml | content % | Concentration mg/100 ml | content % | Concentration mg/100 ml | content % | Concentration mg/100 ml | content % |
| UB | 25° C. | 20.79 | 99.00 | 20.83 | 99.20 | 20.92 | 99.62 | 20.85 | 99.29 |
| | 40° C. | | | 20.78 | 98.96 | 20.70 | 98.57 | 20.75 | 98.79 |
| VT | 25° C. | 10.82 | 98.36 | 10.85 | 98.63 | 10.82 | 98.36 | 10.58 | 96.21 |
| | 40° C. | | | 10.44 | 94.92 | 9.95 | 90.45 | 9.48 | 86.21 |

The components of the self-made sample (sample 13) are described in Table 21.

TABLE 21

Components of Sample 13

| Ingredient | Sample 13 |
|---|---|
| UB | 3.71 mg |
| VT | 2 mg |
| SBECD | 2.5 g |
| NaCl | 300 mg |
| HCl | Adjusted to target pH 4.0 |
| Purified water | Added to 50 g |

Preparation of Sample 13:

Weigh the prescribed amount of NaCl into a beaker and add about 20 g of pure water, stirring with a glass rod to completely dissolve. Add 2.5 g of SBECD to the beaker, then add about 47 g of pure water and stir to dissolve with a glass rod. Adjust the pH to 4.03 with hydrochloric acid. Add the UB and VT and place the resulting mixture on a magnetic stirrer and continue to stir until the components completely dissolve. After the UB and VT are completely dissolved make the solution up to a weight of 50.0 g with pure water.

Determine particle size distribution using the NGI. (Experimental flow rate 15 L/min, experimental atomization device PART e-Flow).

Aerodynamic Particle Size Distribution:

The aerodynamic particle size distribution was determined using a Next Generation Pharmaceutical Impactor (NGI). The device is a PART E-flow, purchased from PART. The device was held close to the NGI inlet until no aerosol was visible. The flow rate of the NGI was set to 15 L/minute and was operated under ambient temperature and a relative humidity (RH) of 90%.

The solution of sample 13 was discharged into the NGI. Fractions of the dose were deposited at different stages of the NGI, in accordance with the particle size of the fraction. Each fraction was washed from the stage and analyzed using HPLC.

The results are shown in Table 22.

TABLE 22

Aerodynamic Particle Size Distribution of Sample 13

| | VT | | UB | | |
|---|---|---|---|---|---|
| Deposited | Dosage (μg) | Percentage content at all levels % | Dosage (μg) | Percentage content at all levels % | Cut-off diameters at 15 L/min (μm) |
| Device | 1.91 | 5.49 | 4.12 | 5.64 | |
| Throat | 0.76 | 2.17 | 0.64 | 0.88 | |
| Stage 1 | 0.38 | 1.08 | 0.82 | 1.13 | 14.10 |
| Stage 2 | 0.76 | 2.18 | 1.63 | 2.24 | 8.61 |
| Stage 3 | 4.01 | 11.51 | 8.50 | 11.65 | 5.39 |
| Stage 4 | 12.46 | 35.74 | 26.11 | 35.81 | 3.30 |
| Stage 5 | 11.45 | 32.83 | 24.12 | 33.07 | 2.08 |
| Stage 6 | 1.87 | 5.35 | 3.97 | 5.45 | 1.36 |
| Stage 7 | 0.85 | 2.45 | 1.77 | 2.42 | 0.98 |
| Moc | 0.04 | 0.11 | 0 | 0 | |
| Stage F | 0.38 | 1.09 | 1.24 | 1.70 | |
| MMAD (μm) | 3.48 | | 3.48 | | |
| GSD | 1.55 | | 1.55 | | |
| ISM (μg) | 31.82 | | 67.35 | | |
| Theoretical Dose (μg) | 40 | | 74.2 | | |
| Actual detection dose (μg) | 34.87 | | 72.93 | | |
| Recovery rate (%) | 87.18 | | 98.27 | | |
| FPF (%) | 77.57 | | 78.46 | | |
| FPD (μg) | 27.05 | | 57.22 | | |

MOC is Micro-Orifice Collector.

ISM is Impactor Size Mass.

FPF is Fine Particle Fraction.

MMAD is mass median aerodynamic diameter.

GSD is Geometric Standard Deviation.

Stage F is filter, which is a DDU tube connected to the end of the NGI.

Comparison Experiment:

The NGI was used to characterize the aerosol from the original ANORO ELLIPTA formulation of umeclidinium bromide and vilanterol trifenatate inhalation powder, purchased from Glaxo Operations UK. Ltd. Each released dose contained 40 microgram of VT and 74.2 microgram of UB. the NGI. The results are provided in Table 23. Perform the NGI test (Experimental flow rate 30 L/min, experimental atomization device is the device that comes with the ANORO ELLIPTA formulation).

TABLE 23

Aerodynamic Particle Size Distribution of ANORO ELLIPTA

| | VT | | UB | | |
|---|---|---|---|---|---|
| | Dosage (μg) | Percentage content at all levels % | Dosage (μg) | Percentage content at all levels % | Cut-off diameters at 30 L/min (μm) |
| Pre-separator | 10.26 | 25.54 | 16.61 | 20.66 | |
| Throat | 6.74 | 16.78 | 15.37 | 19.12 | |
| S1 | 0.45 | 1.13 | 1.07 | 1.34 | 11.72 |
| S2 | 1.23 | 3.06 | 3.94 | 4.9 | 6.40 |
| S3 | 1.7 | 4.22 | 9.78 | 12.16 | 3.99 |
| S4 | 6.96 | 17.34 | 16.79 | 20.88 | 2.30 |
| S5 | 7.38 | 18.38 | 10.54 | 13.12 | 1.36 |
| S6 | 3.6 | 8.98 | 4.31 | 5.37 | 0.83 |
| S7 | 1.1 | 2.75 | 1.3 | 1.61 | 0.54 |
| MOC | 0.73 | 1.83 | 0.68 | 0.84 | |
| MMAD (μm) | 2.12 | | 2.92 | | |
| GSD | 1.84 | | 1.84 | | |
| ISM(μg) | 22.71 | | 47.34 | | |
| Theoretical Dose (μg) | 40 | | 74.2 | | |
| Actual detection dose (μg) | 40.15 | | 80.39 | | |
| Recovery rate (%) | 100.4 | | 108.3 | | |
| FPF (%) | 53.50 | | 53.99 | | |
| FPD(μg) | 21.48 | | 43.40 | | |

S1 is Stage 1

Comparing the NGI parameters of the ANORO ELLIPTA formulation and the self-made formulation, it can be seen that the effective lung deposition of the self-made formulation is much higher than that of the ANORO ELLIPTA formulation, indicating that the bioavailability of the self-made formulation sprayed with an E-flow device is higher.

The results of the NGI analysis show that most of the active ingredients are distributed in S3 to S5, showing that the formulation of the invention provides good lung deposition.

Because the ISM of the self-made formulation is much higher than that of the original research, in order to be consistent with the original research, it is considered that the effective dose of vilanterol trifenatate and umeclidinium bromide can be reduced. In one embodiment, the daily dose of UB is about 55.7 micrograms and the daily dose of VT is about 30 micrograms.

What is claimed is:

1. A liquid, propellant-free pharmaceutical formulation comprising:
   (a) umeclidinium bromide and vilanterol trifenatate;
   (b) a solvent;
   (c) a pharmacologically acceptable solubilizing agent, wherein the pH of the formulation ranges from about 2.5 to about 6.

2. The pharmaceutical formulation of claim 1, wherein the umeclidinium bromide is present in an amount ranging from about 2 mg/100 ml to about 1050 mg/100 ml.

3. The pharmaceutical formulation of claim 1, wherein the vilanterol trifenatate is present in an amount ranging from about 1 mg/100 ml to about 550 mg/100 ml.

4. The pharmaceutical formulation of claim 1, wherein the solvent is water.

5. The pharmaceutical formulation of claim 1, wherein the solubilizing agent is selected from the group consisting of tween-80 and cyclodextrin derivatives.

6. The pharmaceutical formulation of claim 1, wherein the solubilizing agent is present in an amount ranging from about 1 g/100 ml to about 40 g/100 ml.

7. The pharmaceutical formulation of claim 6, wherein the solubilizing agent is sulfobutylether β-cyclodextrin in an amount ranging from about 1 g/100 ml to about 40 g/100 ml.

8. The pharmaceutical formulation of claim 1, further comprising a preservative selected from the group consisting of benzalkonium chloride, benzoic acid, and sodium benzoate.

9. The pharmaceutical formulation of claim 8, wherein the preservative is present in an amount ranging from about 2 mg/100 ml to about 300 mg/100 ml.

10. The pharmaceutical formulation of claim 1, further comprising a stabilizer selected from the group consisting of edetic acid, edetate disodium dehydrate, edetate disodium, citric acid, and combinations thereof.

11. The pharmaceutical formulation of claim 1, wherein the stabilizer is present in an amount ranging from about 1 mg/100 ml to about 500 mg/100 ml.

12. A method for administering the pharmaceutical formulation of claim 1 comprising nebulizing a defined amount of the pharmaceutical formulation with an inhaler by using pressure to force the pharmaceutical preparation through a nozzle to form an inhalable aerosol.

13. The method of claim 12, wherein the defined amount of the pharmaceutical formulation is less than about 70 microliters.

14. The method of claim 12, wherein the mass median aerodynamic diameter (MMAD) of vilanterol trifenatate and umeclidinium bromide are less than about 10 μm.

15. The method of claim 12, wherein the geometric standard deviation (GSD) of vilanterol trifenatate and umeclidinium bromide are less than about 5%.

16. The method of claim 12, wherein the aerosol has a particle size distribution having a Dv(10) of less than about 4 μm, a Dv(50) of less than about 7 μm, and a Dv(90) of less than about 12 μm.

17. The method of claim 12, wherein the pharmaceutical formulation is administered using an inhaler as depicted in FIG. 1.

18. A method of treating asthma or COPD in a patient, comprising administering to the patient the pharmaceutical formulation of claim 1 by inhalation.

19. The method of claim 18, wherein the daily dose of umeclidinium bromide is about 15 micrograms to about 110 micrograms and the daily dose of vilanterol trifenatate is about 9 micrograms to about 60 micrograms.

20. A liquid, propellant-free pharmaceutical formulation comprising:
   an aqueous solution of:
     (a) umeclidinium bromide in an amount of about 2 mg/100 mL to about 1050 mg/100 mL of the formulation;
     (b) vilanterol trifenatate in an amount of about 1 mg/100 mL to about 550 mg/100 mL of the formulation;
     (c) sulfobutylether β-cyclodextrin (SBECD) in an amount of about 1 g/100 mL to about 40 g/100 mL of the formulation;
     (d) sodium chloride in an amount of about 100 mg/100 mL to about 900 mg/100 mL of the formulation;
   wherein the pH of the solution ranges from about 2.5 to about 6.

\* \* \* \* \*